United States Patent
Hardacre et al.

(10) Patent No.: US 9,856,422 B2
(45) Date of Patent: Jan. 2, 2018

(54) PROCESS FOR REMOVING NAPHTHENIC ACIDS FROM CRUDE OIL AND CRUDE OIL DISTILLATES

(75) Inventors: Christopher Hardacre, Belfast (GB); Peter Goodrich, Belfast (GB); Azlan Hussain, Belfast (GB); David Rooney, Belfast (GB)

(73) Assignee: The Queen's University of Belfast (GB)

( * ) Notice: Subject to any disclaimer, the term of this patent is extended or adjusted under 35 U.S.C. 154(b) by 842 days.

(21) Appl. No.: 13/989,154

(22) PCT Filed: Nov. 23, 2011

(86) PCT No.: PCT/GB2011/052304
§ 371 (c)(1),
(2), (4) Date: Dec. 12, 2013

(87) PCT Pub. No.: WO2012/069832
PCT Pub. Date: May 31, 2012

(65) Prior Publication Data
US 2014/0091008 A1 Apr. 3, 2014

(30) Foreign Application Priority Data
Nov. 25, 2010 (GB) .................................. 1020029.3

(51) Int. Cl.
| | | |
|---|---|---|
| *C10G 21/16* | (2006.01) | |
| *C10G 21/28* | (2006.01) | |
| *C07C 51/48* | (2006.01) | |
| *C07C 51/47* | (2006.01) | |
| *C10G 19/02* | (2006.01) | |
| *C10G 21/27* | (2006.01) | |
| *C07C 211/63* | (2006.01) | |

(52) U.S. Cl.
CPC .............. *C10G 21/16* (2013.01); *C07C 51/48* (2013.01); *C07C 211/63* (2013.01); *C10G 19/02* (2013.01); *C10G 21/27* (2013.01); *C10G 21/28* (2013.01); *C10G 2300/104* (2013.01); *C10G 2300/1033* (2013.01); *C10G 2300/1051* (2013.01); *C10G 2300/1055* (2013.01); *C10G 2300/1059* (2013.01); *C10G 2300/203* (2013.01); *Y02P 20/582* (2015.11)

(58) Field of Classification Search
CPC ....... C07C 51/48; C07C 63/36; C07C 211/63; C10G 19/02; C10G 21/06; C10G 21/16; C10G 21/27; C10G 21/28; C10G 2300/1033; C10G 2300/104; C10G 2300/1051; C10G 2300/1055; C10G 2300/1059; C10G 2300/20
See application file for complete search history.

(56) References Cited

U.S. PATENT DOCUMENTS

| | | | |
|---|---|---|---|
| 4,199,440 A | 4/1980 | Verachtert | 208/230 |
| 4,959,158 A | 9/1990 | Meikrantz | 210/787 |
| 5,571,070 A | 11/1996 | Meikrantz et al. | 494/22 |
| 5,591,340 A | 1/1997 | Meikrantz et al. | 210/512.3 |
| 5,762,800 A | 6/1998 | Meikrantz et al. | 210/512.3 |
| 2002/0169071 A1 | 11/2002 | Sauvage et al. | 502/150 |
| 2002/0198100 A1 | 12/2002 | Mehnert et al. | 502/150 |
| 2003/0085156 A1 | 5/2003 | Schoonover | 208/230 |
| 2006/0070919 A1 | 4/2006 | Vallee et al. | 208/298 |
| 2008/0306319 A1 | 12/2008 | Earle et al. | 585/516 |

FOREIGN PATENT DOCUMENTS

| | | | | |
|---|---|---|---|---|
| CN | 1914181 | | 2/2007 | |
| GB | WO 2007138307 A2 | * | 12/2007 | C10G 21/27 |
| GB | 0908986 | * | 7/2009 | C10G 21/27 |
| WO | 99/12650 | | 3/1999 | B04B 1/04 |
| WO | 00/29120 | | 5/2000 | B04B 1/04 |
| WO | 00/46322 | | 8/2000 | C10G 21/12 |

OTHER PUBLICATIONS

Smiglak, M, et al., New Hydrogen Carbonate Precursors for Efficient and Byproduct-free Synthesis of Ionic Liquids based on 1,2,3,-trimethylimidazolium and N,N-dimethylpryrrolidinium Cores, 2010, Green Chemistry, vol. 12, pp. 491-501.*
East entry evidencing publication date of Great Britian Application 0908986.*

* cited by examiner

*Primary Examiner* — Renee Robinson
*Assistant Examiner* — Derek Mueller
(74) *Attorney, Agent, or Firm* — Ryan T. Grace; Advent, LLP

(57) ABSTRACT

The present invention relates to a process for the removal of naphthenic acids from crude oils and crude oil distillates by use of supported basic ionic liquids.

23 Claims, No Drawings

PROCESS FOR REMOVING NAPHTHENIC ACIDS FROM CRUDE OIL AND CRUDE OIL DISTILLATES

The present invention relates to a process for the removal of naphthenic acids from crude oils and crude oil distillates.

Naphthenic acids are carboxylic acids found in crude oil and in various crude oil distillates during the refining of crude oils. The term "naphthenic acids" encompasses a large number of carboxylic acid compounds comprising one or more cycloalkyl rings and having a molecular weight in the range of from about 120 to well over 700. The majority of naphthenic acids found in crude oils and crude oil distillates have a carbon backbone comprising 9 to 20 carbon atoms and cyclopentyl rings are the predominant cycloalkyl ring structure, although other cycloalkyl rings, such as cyclohexyl and cycloheptyl rings may be present in appreciable amounts.

The presence of acidic impurities in crude oil and crude oil distillates causes corrosion of pipelines and distillation equipment at the elevated temperatures used in oil refineries (greater than 200° C.), and acidic crude oils and crude oil distillates have reduced market value compared to crude oils and crude oil distillates of low acidity. Accordingly, effective methods are required to reduce the naphthenic acid content of crude oils and crude oil distillates.

The acidity of crude oils and crude oil distillates is measured in terms of the Total Acid Number (TAN) in accordance with ASTM D0664. The Total Acid Number is the amount of potassium hydroxide in milligrams that is needed to neutralize the acid in one gram of oil, with values in excess of 0.5 mg KOH/g being indicative of high acidity. Typical TAN values for acidic crude oils and crude oil distillates are in the range of 0.5 to 4.0 mg KOH/g, while acidic distillate fractions such as kerosene may have TAN values in the range of, for example, 0.5 to 8.0 mg KOH/g.

Various methods for deacidifying crude oil and crude oil distillates are known. In a conventional deacidification process, an alkali such as aqueous sodium hydroxide or aqueous potassium hydroxide is contacted with the oil to neutralize any acid present. The reaction produces an aqueous phase comprising water, and alkali metal salt. This aqueous phase has to be removed from the deacidified oil before the oil can be used or sold. According to U.S. Pat. No. 4,199,440, a problem arises in that alkali metal compounds are chemically similar to soap, and tend to emulsify hydrocarbon and aqueous phases. This emulsion interferes with the efficient separation of the deacidified oil and aqueous phase.

A further example of a crude oil deacidification process is described in WO 00/46322. In this application, a crude oil is contacted with a polar solvent (for example, methanol), such that at least part of the acid present in the oil is extracted into the solvent as an extract phase. The extract phase is then separated from the oil. However, a problem with this process is that a certain number of the acid impurities are not extractable into the solvent. A further problem is that the acid partitions between the oil and the extract phase such that high amounts of polar solvent and repeated extractions are required to reduce the acid content of the oil to an acceptable level. This has the further disadvantage that large volumes of polar solvent must be regenerated for recycling to the extraction stage.

One aspect of this invention is based on the discovery that specifically selected ionic liquids may be used to remove naphthenic acids from crude oils and crude oil distillates more efficiently than in prior art deacidification processes.

Ionic liquids are a novel class of compounds which have been developed over the last few years. The term "ionic liquid" as used herein refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., preferably below 150° C., particularly below 100° C., around room temperature (15 to 30° C.), or even below 0° C. Ionic liquids having melting points below around 30° C. are commonly referred to as "room temperature ionic liquids" and are often derived from organic salts having nitrogen-containing heterocyclic cations, such as imidazolium and pyridinium-based cations. In room temperature ionic liquids, the structures of the cation and anion prevent the formation of an ordered crystalline structure and therefore the salt is liquid at room temperature.

Ionic liquids are most widely known as solvents, because their negligible vapour pressure, temperature stability, low flammability and recyclability make them environmentally friendly. Due to the vast number of anion/cation combinations that are available it is possible to fine-tune the physical properties of the ionic liquid (e.g. melting point, density, viscosity, and miscibility with water or organic solvents) to suit the requirements of a particular application.

According to US 2003/0085156 ionic liquids may be used in the removal of organosulfur compounds, such as mercaptans, sulfides, disulfides, thiophenes, benzothiophenes and dibenzothiophenes, from hydrocarbon materials via countercurrent contact between a hydrocarbon stream and an ionic liquid. In the examples disclosed, very large quantities of ionic liquid are required, for example, 2 ml of ionic liquid per 2 ml of hydrocarbon, i.e. a 1:1 ratio.

US 2006/0070919 is concerned with the processing of Fischer-Tropsch synthesis effluents and more particularly alcohols and acids formed during such a reaction. Similar to US 2003/0085156, very large quantities of ionic liquid were required, for example, 2 ml of ionic liquid per 4 ml of hydrocarbon, in order to demonstrate satisfactory results.

It is readily apparent that such large quantities are not practical for commercial application, and indeed would be prohibitively expensive to operate.

In accordance with the present invention, there is provided a process for removing organic acids from a crude oil and/or a crude oil distillate containing organic acids comprising the steps of:
  (i) contacting the crude oil and/or the crude oil distillate containing organic acids with a supported basic ionic liquid having a basic anion selected from alkylcarbonate or hydrogen carbonate wherein the ionic liquid and the crude oil and/or crude oil distillate are contacted in a mass ratio of from greater than 1:40; and
  (ii) obtaining a crude oil and/or crude oil distillate product having reduced acidity which is separated from the supported basic ionic liquid.

The present inventors has found that the use of a supported basic ionic liquid having a basic anion selected from alkylcarbonate or hydrogencarbonate allows a crude oil/crude oil distillate to be more efficiently processed, such that a mass ratio of basic ionic liquid to crude oil/crude oil distillate of greater than 1:40 may be used.

Examples of organic acids that may be present in the crude oil/crude oil distillate include phenolic acids, sulphur-containing acids, and most commonly, naphthenic acids. Preferably, the processes of the present invention are for the removal of naphthenic acids.

The process of the present invention is effective at ratios of basic ionic liquid to crude oil and/or the crude oil distillate in mass ratios of up to 1:200, and 1:300, and even greater than 1:300.

The ionic liquid and the crude oil and/or the crude oil distillate may be contacted in a mass ratio of from 1:50, and from 1:100, and also from 1:150.

In a preferred embodiment of the present invention, the basic anion is selected from alkylcarbonate. More preferably the alkyl group may be linear or branched, and/or may additionally be substituted or unsubstituted.

In one preferred embodiment the alkyl group is unsubstituted.

In another preferred embodiment the alkyl group is unbranched.

In a more preferred embodiment the alkyl group is unsubstituted and unbranched.

In the embodiments of the present invention, the alkyl group may comprise from 1 to 30 carbon atoms, preferably from 1 to 20 carbon atoms and more preferably form 1 to 10 carbon atoms.

The alkyl groups may be selected from one or more of methyl, ethyl, propyl, butyl, pentyl, hexyl, heptyl, octyl, nonyl and/or decyl.

Especially preferred are methyl, ethyl, propyl, butyl and pentyl.

In a further preferred embodiment the alkyl groups are selected from methyl and ethyl.

It will be understood that branched alkyl groups such as iso-propyl, iso-butyl, sec-butyl and/or tert-butyl may also be used.

Suitable supports for use in the present invention may be selected from silica, alumina, carbon, zirconia, alumina-silica, or a zeolite. Preferably, the support is silica.

Methods for supporting an ionic liquid on a support material are well known in the art, such for example, in US 2002/0169071, US 2002/0198100 and US 2008/0306319. Typically, the basic ionic liquid may be physisorbed or chemisorbed on the support material, preferably, chemisorbed. The ionic liquids may also be covalently bonded to the support material as described in further detail below.

In the processes of the present invention, the ionic liquid may adsorbed onto the support in an ionic liquid:support mass ratio of from 10:1 to 1:10, preferably in an ionic liquid:support mass ratio of from 1:2 to 2:1.

In accordance with a further aspect of the present invention, there is provided a process for removing organic acids, such as those described above, and preferably naphthenic acids, from a crude oil and/or a crude oil distillate containing organic acids comprising the steps of:
(i) contacting the crude oil and/or the crude oil distillate containing organic acids with a basic ionic liquid having a basic anion selected from alkylcarbonate (such as those described above) and hydrogencarbonate, and further wherein the ionic liquid and the crude oil and/or crude oil distillate are contacted in a mass ratio of from greater than 1:40; and
(ii) obtaining a crude oil and/or crude oil distillate product having reduced acidity which is separated from the supported basic ionic liquid.

In the further aspect, the mass ratios of basic ionic liquid to crude oil and/or the crude oil distillate may be up to 1:100, and 1:125, and even up to 1:150. The ionic liquid and the crude oil and/or the crude oil distillate may be contacted in a mass ratio of from 1:50, and from 1:75, and also from 1:100.

The processes of the present inventions as described herein are able to obtain crude oil/crude oil distillates having a TAN value of less than 0.25 mg/g, preferably less than 0.2 mg/g, more preferably less than 0.1 mg/g, still more preferably less than 0.075 mg/g and most preferably less than 0.05 mg/g.

In the further aspect, the basic ionic liquid preferably has a melting point of less than 150° C., and more preferably less than 100° C. Alternatively, an ionic with a higher melting point, i.e. greater than 20° C., preferably greater than 100° C., and more preferably greater than 150° C. may be used where it is intended to contact a solid ionic liquid with the crude oil/crude oil distillate.

In the processes of the present inventions, the basic ionic liquid may comprise a cation selected or derived from the group consisting of: ammonium, azaannulenium, azathiazolium, benzimidazolium, benzofuranium, benzotriazolium, borolium, cinnolinium, diazabicyclodecenium, diazabicyclononenium, diazabicyclo-undecenium, dithiazolium, furanium, imidazolium, indazolium, indolinium, indolium, morpholinium, oxaborolium, oxaphospholium, oxazinium, oxazolium, iso-oxazolium, oxothiazolium, pentazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenozolium, sulfonium, tetrazolium, iso-thiadiazolium, thiazinium, thiazolium, thiophenium, triazadecenium, triazinium, triazolium, and iso-triazolium.

In one embodiment, the cation may be selected from the group consisting of:

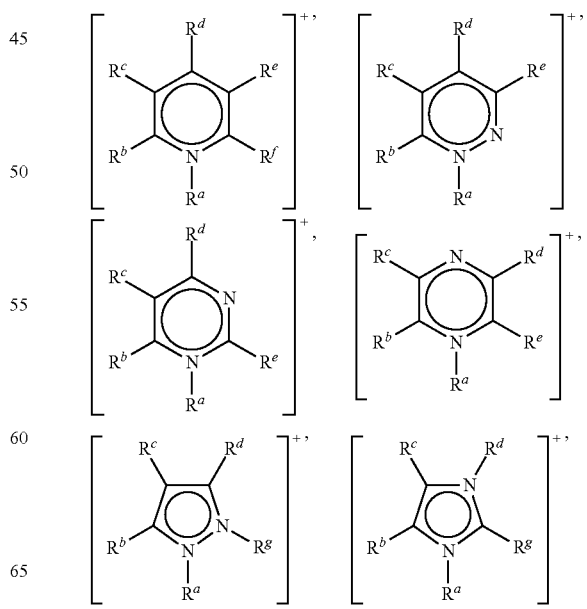

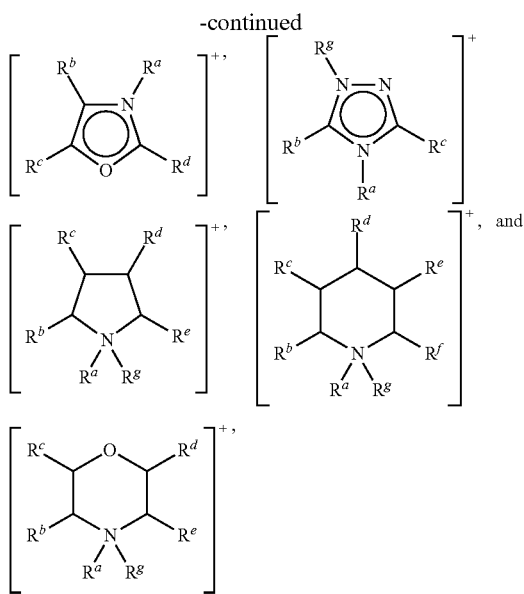

wherein:
$R^a$, $R^b$, $R^c$, $R^d$, $R^e$, $R^f$ and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —NO$_2$, $C_6$ to $C_{10}$ aryl and $C_7$ to $C_{10}$ alkaryl, —CO$_2$($C_1$ to $C_6$)alkyl, —OC(O)($C_1$ to $C_6$)alkyl, or any two of $R^b$, $R^c$, $R^d$, $R^e$ and $R^f$ attached to adjacent carbon atoms form a methylene chain —(CH$_2$)$_q$— wherein q is from 3 to 6.

Preferably, $R^a$, $R^b$, $R^c$, $R^d$, $R^e$, $R^f$ and $R^g$ are each independently selected from a $C_1$ to $C_{20}$ straight chain or branched alkyl group, a $C_3$ to $C_6$ cycloalkyl group, or a $C_6$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —NO$_2$, —CO$_2$($C_1$ to $C_6$)alkyl, —OC(O)($C_1$ to $C_6$)alkyl, $C_6$ to $C_{10}$ aryl and $C_7$ to $C_{10}$ alkaryl, and wherein one of $R^b$, $R^c$, $R^d$, $R^e$, $R^f$ and $R^g$ may also be hydrogen.

$R^a$ is preferably selected from $C_1$ to $C_{30}$, linear or branched, alkyl, more preferably $C_2$ to $C_{20}$ linear or branched alkyl, still more preferably, $C_2$ to $C_{10}$ linear or branched alkyl, and most preferably $R^a$ is selected from ethyl, n-butyl, n-hexyl and n-octyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_2$ to $C_{20}$ linear or branched alkyl, still more preferably, $C_2$ to $C_{10}$ linear or branched alkyl, and most preferably $C_4$ to $C_8$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_{15}$ alkoxyalkyl.

In another embodiment, the cation may be selected from the group consisting of:

$[N(R^a)(R^b)(R^c)(R^d)]^+$, $[P(R^a)(R^b)(R^c)(R^d)]^+$, and $[S(R^a)(R^b)(R^c)]^+$, wherein:
$R^a$, $R^b$, $R^c$ and $R^d$ are as defined above.
Preferably, the cation is selected from:

$[N(R^a)(R^b)(R^c)(R^d)]^+$, wherein:
$R^a$, $R^b$, $R^c$ and $R^d$ are each independently selected from $C_1$ to $C_8$ alkyl, including $C_2$, $C_4$ and $C_6$ alkyl.

In the processes of the present inventions, the term "crude oil or a crude oil distillate" is intended to include liquefied petroleum gas, gasoline, gas oil, naphtha, kerosene, diesel fuel, fuel oil, jet fuel, home heating oil, lubricating oil or paraffin wax, or mixtures thereof.

In the processes of the present inventions, the basic ionic liquid may additionally comprise a basic cation represented by the formula:

Cat$^+$-(Z-Bas)$_n$ wherein:
Cat$^+$ is a positively charged moiety;
Bas is a basic moiety;
Z is a covalent bond joining Cat$^+$ and Bas, or is a divalent linking group; and
n is an integer of from 1 to 3, and preferably n is 1.

Suitably, Bas comprises at least one basic nitrogen, phosphorus, sulfur, or oxygen atom, preferably, at least one basic nitrogen atom.

Bas may comprise a heterocyclic ring system containing a basic nitrogen atom, a pyrrolidine or a piperidine ring Preferably, Bas is selected from —N(R$^1$)(R$^2$), —P(R$^1$)(R$^2$) and —S(R$^3$). Bas may also be —O(R$^3$). Suitably, R$^1$ and R$^2$ are independently selected from hydrogen, linear or branched alkyl, cycloalkyl, aryl and substituted aryl, or, in the case of an —N(R$^1$)(R$^2$) group, R$^1$ and R$^2$ together with the interjacent nitrogen atom form part of a heterocyclic ring. Suitably, R$^3$ is selected from linear or branched alkyl, cycloalkyl, aryl and substituted aryl.

Preferably, R$^1$, R$^2$ and R$^3$ are selected from methyl, ethyl, n-propyl, isopropyl, n-butyl, iso-butyl, tert-butyl, n-pentyl, n-hexyl, cyclohexyl, benzyl and phenyl, or, in the case of an —N(R$^1$)(R$^2$) group, R$^1$ and R$^2$ together represent a tetramethylene or pentamethylene group optionally substituted by one or more $C_{1-4}$ alkyl groups.

Preferably, the basic moiety is a "hindered basic group" i.e. is a functional group that acts as a base and, owing to steric hindrance, does not chemically bond to any of the components of the oil (other of course than by accepting a proton in the usual reaction of a Brønsted acid with a Brønsted base). Suitable hindered basic groups include —N(CH(CH$_3$)$_2$)$_2$ and —N(C(CH$_3$)$_3$)$_2$. Preferably, the hindered basic group has a lower nucleophilicity (or greater steric hindrance) than N(C$_2$H$_5$)$_3$.

In the context of the present invention, the group —OH is not considered basic due to difficulties with protonation.

Accordingly, Bas as defined herein does not include —OH, and in a preferred embodiment, does not include —O(R$^3$).

Z may be a divalent organic radical having from 1 to 18 carbon atoms, preferably 1 to 8 carbon atoms, more preferably, 2 to 6 carbon atoms. The divalent organic radical, Z, may be branched or unbranched. The divalent organic radical, Z, may be substituted or unsubstituted. Preferably, the valence bonds are on different carbon atoms of the divalent organic radical, Z.

Suitably, the divalent organic radical, Z, is a divalent aliphatic radical (for example, alkylene, alkenylene, cycloalkylene, oxyalkylene, oxyalkyleneoxy, alkyleneoxyalkylene or a polyoxyalkylene) or is a divalent aromatic radical (for example, arylene, alkylenearylene or alkylenearylenealkylene).

Preferably, Z is:
(a) a divalent alkylene radical selected from: —(CH$_2$—CH$_2$)—, (CH$_2$—CH$_2$—CH$_2$)—, —(CH$_2$—CH$_2$—CH$_2$—CH$_2$)—, —(CH$_2$—CH$_2$—CH$_2$—CH$_2$—CH$_2$)—, —(CH$_2$—CH$_2$—CH$_2$—CH$_2$—CH$_2$—CH$_2$)—, —(CH$_2$—CH(CH$_3$))—, and —(CH$_2$—CH(CH$_3$)—CH$_2$—CH(CH$_3$))—;
(b) a divalent alkyleneoxyalkylene radical selected from: —(CH$_2$—CH$_2$—O—CH$_2$—CH$_2$)—, —(CH$_2$—CH$_2$—O—CH$_2$—CH$_2$—CH$_2$)—, and —(CH$_2$—CH(CH$_3$)—O—CH$_2$—CH(CH$_3$))—;
(c) a divalent polyoxyethylene radical selected from: —(CH$_2$CH$_2$O)$_n$— where n is an integer in the range 1 to 9 or —(CH$_2$CH(CH$_3$)O)$_m$— where m is an integer in the range 1 to 6; and
(d) a divalent alkylenearylene or an alkylenearylenealkylene radical selected from: —(CH$_2$—C$_6$H$_4$)—, and —(CH$_2$—C$_6$H$_4$—CH$_2$)—.

The Cat$^+$ moiety may comprise a heterocyclic ring structure selected from imidazolium, pyridinium, pyrazolium, thiazolium, isothiazolinium, azathiozolium, oxothiazolium, oxazinium, oxazolium, oxaborolium, dithiozolium, triazolium, selenozolium, oxaphospholium, pyrollium, borolium, furanium, thiophenium, phospholium, pentazolium, indolium, indolinium, oxazolium, isooxazolium, isotriazolium, tetrazolium, benzofuranium, dibenzofuranium, benzothiophenium, dibenzothiophenium, thiadiazolium, pyrimidinium, pyrazinium, pyridazinium, piperazinium, piperidinium, morpholinium, pyranium, annolinium, phthalazinium, quinazolinium, quinazalinium, quinolinium, isoquinolinium, thazinium, oxazinium and azaannulenium.

Examples of Cat$^+$-Z-Bas where Cat$^+$ is a heterocyclic ring structure include:

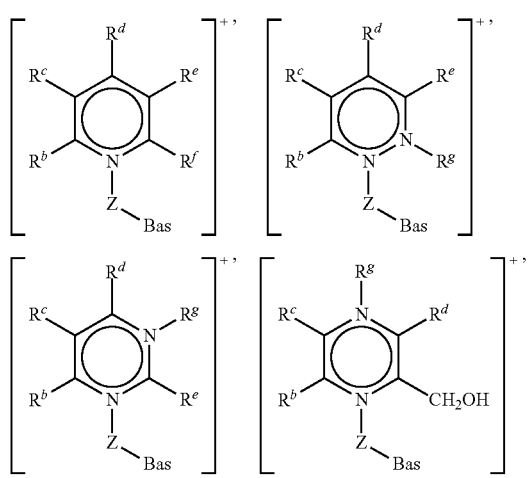

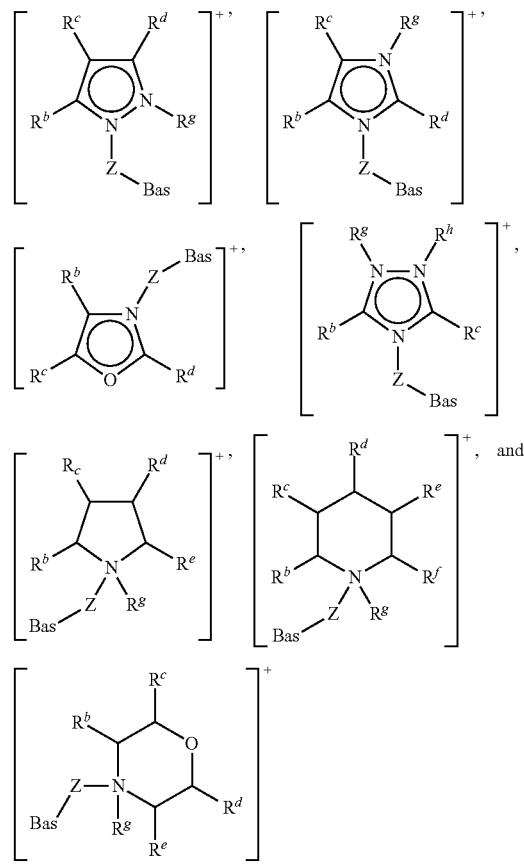

wherein: Bas and Z are as defined above; and R$^b$, R$^c$, R$^d$, R$^e$, R$^f$, R$^g$ and R$^h$ are independently selected from hydrogen, a C$_1$ to C$_{40}$, straight chain or branched alkyl group, a C$_3$ to C$_8$ cycloalkyl group, or a C$_6$ to C$_{10}$ aryl group, wherein said alkyl, cycloalkyl or aryl groups are unsubstituted or may be substituted by one to three groups selected from: C$_1$ to C$_6$ alkoxy, C$_6$ to C$_{10}$ aryl, CN, OH, NO$_2$, C$_7$ to C$_{30}$ aralkyl and C$_7$ to C$_{30}$ alkaryl, or any two of R$^b$, R$^c$, R$^d$, R$^e$ and R$^f$ attached to adjacent carbon atoms on the ring structure form a methylene chain —(CH$_2$)$_p$— wherein p is an integer from 3 to 5.

Preferred Cat$^+$-Z-Bas, where Cat$^+$ is a heterocyclic ring structure, includes:

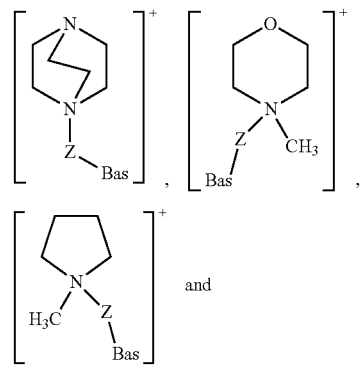

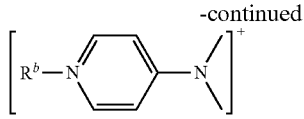

wherein: Bas, Z and $R^b$ are as defined above.

It is particularly preferred that $Cat^+$ is a heterocyclic ring structure and Bas is a sterically hindered amino group, for example:

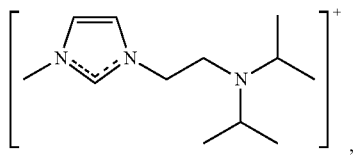

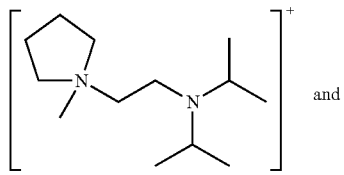

and

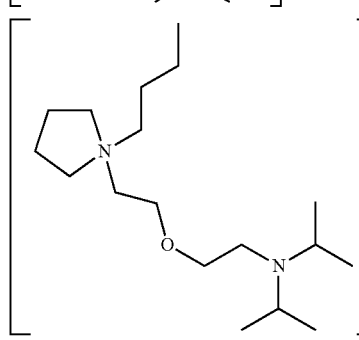

The heterocyclic $Cat^+$ moiety may be obtained by alkylation, protonation and/or acylation of a precursor selected from imidazoles, pyridines, pyrazoles, thiazoles, isothiazoles, azathiozoles, oxothiazoles, oxazines, oxazolines, oxazoboroles, dithiozoles, triazoles, selenozoles, oxaphospholes, pyrroles, boroles, furans, thiophenes, phospholes, pentazoles, indoles, indolines, oxazoles, isooxazoles, isotriazoles, tetrazoles, benzofurans, dibenzofurans, benzothiophenes, dibenzothiophenes, thiadiazoles, pyrimidines, pyrazines, pyridazines, piperazines, piperidines, morpholenes, pyrans, annolines, phthalzines, quinazolines, quinoxalines, quinolines, isoquinolines, thazines, oxazines, and azaannulenes.

It is also envisaged that the $Cat^+$ moiety may be an acyclic hydrocarbyl moiety. Preferably, the acyclic hydrocarbyl moiety comprises a group selected from amino amidino, imino, guanidino, phosphino, arsino, stibino, alkoxyalkyl, alkylthio, alkylseleno and phosphinimino.

Where the $Cat^+$ moiety is an acyclic hydrocarbyl moiety, $[Cat^+-Z-Bas]$ is preferably selected from:

[N(Z-Bas)($R^b$)($R^c$)($R^d$)]$^+$ and [P(Z-Bas)($R^b$)($R^c$)($R^d$)]$^+$ wherein: Bas, Z, $R^b$, $R^c$, and $R^d$ are as defined above. It is particularly preferred that $R^b$, $R^c$, and $R^d$ are independently selected from methyl and ethyl.

Examples of preferred $[Cat^+-Z-Bas]$ of this class include:

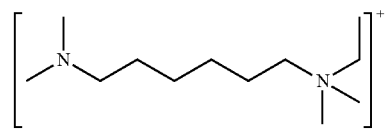
, and

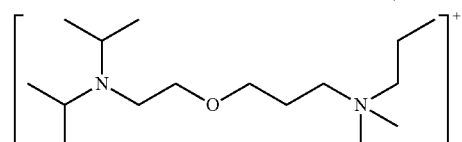
,

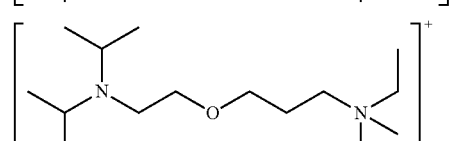
,

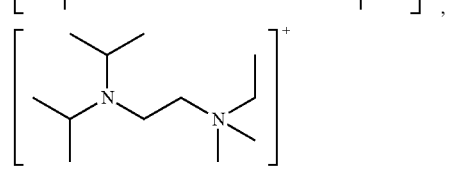
,

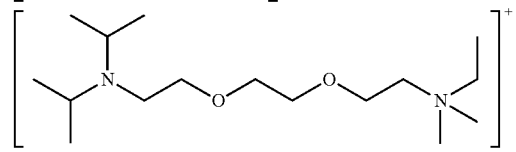

where Bas is the sterically hindered amino group, —N(CH($CH_3$)$_2$)$_2$.

$[Cat^+-Z-Bas]$ may also be:

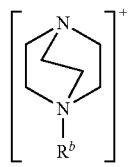

wherein: $R^b$ is as defined above.

Where the basic ionic liquid is unsupported, it is preferably immiscible with the oil. By immiscible with the oil is meant that the basic ionic liquid is soluble in the treated oil phase at a concentration of less than 50 ppm, preferably less than 30 ppm, more preferably less than 20 ppm, most preferably, less than 10 ppm, for example, less than 5 ppm. Thus, the solubility of the basic ionic liquid is tailored so that the basic ionic liquid is immiscible with the oil. The solubility of the basic ionic liquid may also be tailored such that the basic ionic liquid is either insoluble or soluble in water. By insoluble in water is meant that the basic ionic liquid has a solubility in water of less than 50 ppm, preferably, less than 30 ppm, more preferably less than 20 ppm, most preferably, less than 10 ppm, for example, less than 5 ppm.

Suitably, the contacting steps (i), of the processes of the present invention, are carried out at a temperature of from ambient to 150° C. Suitably, the contacting steps (i) are carried out at a pressure of from 0.1 MPa absolute to 10 MPa absolute (1 bar absolute to bar absolute).

Where the ionic liquid is unsupported, step (i) may be carried out by contacting the oil with the basic ionic liquid in a vessel wherein the resulting mixture is stirred using, for example, a mechanical stirrer, an ultrasonic stirrer, an electromagnetic stirrer or by bubbling an inert gas through the mixture. Suitably, the volume ratio of basic ionic liquid to oil in the extraction step is from greater than 1:40 to 1:300, and may be contacted in a mass ratio of from 1:50, preferably from 1:100. The mixing step may last from 1 minute to 60 minutes, preferably 2 to 30 minutes, more preferably, 5 to 20 minutes and most preferably, 8 to 15 minutes.

It will be understood that in the processes (i.e. supported and unsupported ionic liquids) of the present inventions, it is not a requirement that the molar amount of basic ionic liquid employed in the contacting steps (i) be at least equivalent to the molar amount of organic acids in the oil.

Where the basic ionic liquid is water soluble, and the oil to be treated using the process of the present invention has a high water content it may be necessary to dehydrate the oil prior to contacting the oil with the basic ionic liquid in steps (i). The water may be separated from the oil in, for example, a separator or coalescer. Preferably, the concentration of water in the oil is less than 0.5% volume of oil, for example, less than 0.25% volume of oil.

The water removed in the pre-treatment of the oil may itself contain organic acids which can be removed using basic ionic liquids. The present invention therefore also provides a process by which organic acids can be removed from aqueous streams using basic ionic liquids. Such a process is extremely useful in ensuring that waste water effluents from oil processing plants are substantially free of contaminants which are potentially harmful to the environment.

Where the basic ionic liquid is insoluble in water, it is believed that any water present in the mixture (arising from the oil) may be beneficial in achieving the clean separation of the unsupported basic ionic liquid from the treated oil in step (ii). Accordingly, it is not necessary to dehydrate the oil prior to step (i).

For unsupported basic ionic liquids, step (ii) may be carried out by gravity separation, (for example, in a settling unit) where the treated oil is generally the upper phase and the basic ionic liquid the lower phase in the settling unit. Where the unsupported basic ionic liquid is insoluble in water, the presence of the water will result in a 3 phase mixture where the treated oil is generally the upper phase, the water the middle phase and the basic ionic liquid containing the organic acids the lower phase in the settling unit. The phases may also be separated in step (ii) using, for example, a decanter, a hydrocyclone, electrostatic coalescer or a centrifuge. Step (i) followed by step (ii) may be repeated several times, preferably 2 to 6, for example 2 to 4 times, until the level of organic acids in the oil is reduced to an acceptable value.

Steps (i) and (ii) may also be carried out together in a counter-current extraction column. The oil contaminated with the organic-containing acids (hereinafter "oil feed stream") is generally introduced at or near the bottom of the counter-current extraction column and the basic ionic liquid (hereinafter "basic ionic liquid feed stream") at or near the top of the counter-current extraction column. An oil phase which is reduced in acid content (hereinafter "product oil stream") is withdrawn from the top of the column and a basic ionic liquid extract phase containing the extracted acids (hereinafter "extract stream") from at or near the bottom thereof. Preferably, the counter-current extraction column has a sump region for collecting the basic ionic liquid extract phase. Preferably, the oil feed stream is introduced to the counter-current extraction column immediately above the sump region. More than one counter-current extraction column may be employed, for example 2 to 6, preferably 2 to 3 columns arranged in series. Preferably, the counter-current extraction column is packed with a structured packing material, for example, glass Raschig rings, thereby increasing the flow path for the oil and basic ionic liquid through the column. Alternatively, the counter-current extraction column may contain a plurality of trays.

Steps (i) and (ii) may also be carried out together in a centrifugal contact separator, for example, a centrifugal contact separator as described in U.S. Pat. No. 4,959,158, U.S. Pat. No. 5,571,070, U.S. Pat. No. 5,591,340, U.S. Pat. No. 5,762,800, WO 99/12650, and WO 00/29120. Suitable centrifugal contact separators include those supplied by Costner Industries Nevada, Inc. The oil contaminated with organic-containing acids and the basic ionic liquid may be introduced into an annular mixing zone of the centrifugal contact separator. Preferably, the oil, contaminated with the organic-containing acids, and the basic ionic liquid are introduced as separate feed streams into the annular mixing zone. The oil, and basic ionic liquid are rapidly mixed in the annular mixing zone such that at least a portion of the organic-containing acids are extracted from the oil into the basic ionic liquid. The resulting mixture is then passed to a separation zone wherein a centrifugal force is applied to the mixture to produce a clean separation of an oil phase and a basic ionic liquid extract phase. Preferably, a plurality of centrifugal contact separators are used in series, preferably, 2 to 6, for example 2 to 3. Preferably, the oil feed stream is introduced into the first centrifugal contact separator in the series while the basic ionic liquid feed stream is introduced into the last centrifugal contact separator in the series such that oil of progressively decreasing organic-containing acid content is passed from the first through to the last centrifugal contact separator in the series while a basic ionic liquid of progressively increasing organic-containing acid content is passed from the last through to the first centrifugal contact separator in the series. Thus, the basic ionic liquid extract phase is removed from the first centrifugal contact separator and the oil phase of reduced acidity from the last centrifugal contact separator in the series.

The oil phase of reduced acidity (product oil stream) which is isolated from step (ii) may be used directly or may be further processed, for example, by fractional distillation. If necessary, any residual unsupported basic ionic liquid that is present in the treated oil may be recovered by passing the product oil stream through a silica column such that the residual basic ionic liquid is adsorbed onto the silica column. The adsorbed basic ionic liquid may then be washed off the silica column using a solvent for the basic ionic liquid and the basic ionic liquid may be recovered by driving off the solvent at reduced pressure. Alternatively, the oil may be removed from the residual ionic liquid by hot gas stripping using, for example, hot nitrogen gas.

For the supported basic ionic liquids, contacting step (i) and separation step (ii) may also be carried out together by passing the oil through a column packed with a supported basic ionic liquid (i.e. a packed bed arrangement). Thus, the oil containing the organic-containing acids may be passed through a column containing the supported basic ionic liquid. The organic-containing acids will become associated with the supported basic ionic liquid and oil having a reduced acid content will be removed from the column. In addition, or alternatively, a fixed-bed arrangement having a plurality of plates and/or trays may be used.

It will be noted, and indeed it is a further embodiment of the invention, that crude oil and/or crude oil distillates having reduced organic acid content may be separated from the basic ionic liquid containing organic acids by means of a liquid-liquid extraction.

Suitable liquids for this process include liquids which form a two phase mixture with the crude oil and/or crude oil distillate. Non-limiting examples of suitable liquids include water, aqueous solutions and alcohols. More preferably, the alcohols may be selected from methanol and ethanol. Also more preferably, the liquid may be selected from water and brine.

This separation process is also applicable to basic ionic liquids in general, and especially those having basic anions selected from serinate, prolinate, histidinate, threoninate, valinate, asparaginate, taurinate and lysinate.

It will also be appreciated that the processes of the present invention may also be used to remove organic acids from any water present in the hydrocarbon stream. In this way, a further aspect of the present invention is a process for the removal of organic acids from an aqueous stream containing organic acids comprising the steps of:
  (i) contacting the aqueous stream containing organic acids with a basic ionic liquid (supported or unsupported) as defined hereinabove; and
  (ii) obtaining an aqueous stream product having reduced acidity which is separated from the ionic liquid.

The aqueous stream containing organic acids and the basic ionic liquid may contacted in a mass ratio of from greater than 1:40. The mass ratios suitable for this aspect of the invention include those defined above for the processes for removing organic acids from crude oil/crude oil distillate.

Further, embodiments of the processes above for removing organic acids from crude oil/crude oil distillate also apply to this embodiment.

Preferably, the organic acids to be removed are carboxylic acids.

Other suitable basic ionic liquids for use in this aspect of the invention include those having basic anions selected from serinate, prolinate, histidinate, threoninate, valinate, asparaginate, taurinate and lysinate.

The processes of the present inventions may additionally comprise the step of recovering the basic ionic liquid. Recovery of the basic ionic liquid preferably comprises recovering the basic ionic liquid from the organic acids by way of a regeneration process.

The regeneration process preferably comprises:
  (a) contacting the basic ionic liquid with an acid having a pKa of less than 6.75.

The regeneration process preferably further comprises the steps of:
  (b) contacting the mixture of step (a) with a solvent which is immiscible with the basic ionic liquid; and
  (c) separating the solvent from the ionic liquid.

In accordance with another aspect of the present invention, there is provided a process for the regeneration of a basic ionic liquid comprising organic acids from crude oil/crude oil distillate comprising the steps of:
  (a) contacting the basic ionic liquid with an acid having a pKa of less than 6.75;
  (b) contacting the mixture of step (a) with a solvent which is immiscible with the basic ionic liquid; and
  (c) separating the solvent from the ionic liquid.

Preferably, the pKa of the acid is less than 6.25.

Suitable acids for use in the regeneration process are those that meet the pKa requirements above. Preferably, the acid is carbonic acid.

Other suitable regeneration methods include:
  (1) extraction of the organic-containing acids into a solvent that is immiscible with the basic ionic liquid;
  (2) vaporization of the acids at a reduced pressure and at a temperature less than the decomposition temperature of the ionic liquid, preferably, a temperature less than 200° C.;
  (3) reaction of the acids within the basic ionic liquid to form: (i) products that are insoluble in the basic ionic liquid, (ii) products that are more readily extracted into a solvent that is immiscible with the basic ionic liquid, or (iii) volatile products that are more readily separated from the basic ionic liquid;
  (4) gas stripping wherein a hot gas, for example steam or nitrogen is passed through the ionic liquid to volatilize the acids;
  (5) extraction of the acids with a supercritical fluid, for example, liquefied carbon dioxide; and
  (6) membrane separation (polymer-based, ceramic, zeolite and liquid-liquid systems) where the membrane is selectively permeable to the acids; and combinations of these methods.

Preferably, the organic-containing acids contained in the separated basic ionic liquid extract phase are reacted with a Group 1 and/or Group 2 metal hydroxide such that at least a portion of the acids, preferably, substantially all of the acids, are converted into Group 1 and/or Group 2 neutralization salts thereof within the basic ionic liquid. For example, the basic ionic liquid extract phase may be contacted with solid Group 1 and/or Group 2 metal hydroxide. Without wishing to be bound by any theory, it is believed that the neutralization salts formed by the reaction of the Brønsted acid and the Brønsted base may precipitate from the basic ionic liquid and may therefore be readily separated therefrom. Alternatively, where the basic ionic liquid is insoluble in a polar solvent, the neutralization salts may be extracted from the basic ionic liquid extract phase into the polar solvent. By insoluble in the polar solvent is meant that the basic ionic liquid has a solubility in the polar solvent of less than 50 ppm, preferably, less than 30 ppm, more preferably, less than 20 ppm, most preferably, less than 10 ppm, for example, less than 5 ppm. Suitable polar solvents include water and polar organic solvents such as $C_1$ to $C_6$ aliphatic alcohols, in particular, methanol or ethanol. Where the basic ionic liquid is insoluble in the polar solvent, it is preferred to contact the basic ionic liquid extract phase with a solution of the Group 1 and/or Group 2 metal hydroxide in the polar solvent thereby generating a basic ionic liquid phase of reduced organic-containing acid content and a polar solvent extract phase containing the Group 1 and/or Group 2 metal neutralization salts. Where the polar solvent is a polar organic solvent, the volume ratio of polar organic solvent to basic ionic liquid is typically less than 1:1, preferably less than 0.5:1, more preferably, less than 0.25:1, for example, less than 0.1:1. The polar organic solvent may then be recovered by volatilization of the solvent at reduced pressure leaving behind a solid residue comprising the Group 1 and/or Group 2 metal neutralization salts. Accordingly, it is preferred to contact the basic ionic liquid extract phase with the minimum amount of the solution of the Group 1 and/or Group 2 metal hydroxide in the polar organic solvent. Preferably, the polar solvent is water resulting in a waste water stream containing the Group 1 and/or Group 2 metal neutralization salts of the acid. Where the method of the present invention is employed offshore on a hydrocarbon production platform, the water is preferably seawater and the waste water stream may be disposed of by, for example, being injected into a porous subterranean formation (waste water disposal zone). Thus, higher amounts of water may be employed than polar organic solvent.

The Group 1 metal hydroxide may be selected from lithium hydroxide, sodium hydroxide, and potassium hydroxide, preferably, sodium hydroxide. Suitably, the Group IIA metal hydroxide is selected from barium hydroxide, magnesium hydroxide, and calcium hydroxide, preferably, calcium hydroxide. Mixtures of Group 1 and/or Group 2 metal hydroxides may be employed. However, it is preferred to employ a Group 2 metal salt or mixtures thereof owing to the risk of Group 2 metal salts of the acids forming soaps that can interfere with the separation of the polar solvent from the basic ionic liquid. Particularly preferred is calcium hydroxide.

It is envisaged that where the treated oil is a hydrocarbon that has been produced offshore from a porous hydrocarbon bearing formation, that the basic ionic liquid may be contacted with a brine, for example, seawater or a produced water, on a production platform where the pH of the seawater is adjusted using a base to a value of at least 8, preferably at least 10 during the contacting step. Seawater contains naturally occurring Group 1 and Group 2 metal ions in an amount sufficient to complex with the acids contained in the basic ionic liquid. Typically, the pH of the brine may be adjusted to a value in the range 10 to 12 so that the pH of the brine after neutralization of the acids is in the range 4 to 9. The pH of the seawater may be adjusted using a Group 1 and/or 2 metal hydroxide, for example, sodium hydroxide.

Where the basic ionic liquid is insoluble in the polar solvent, it is envisaged that the oil containing the organic-containing acids, the basic ionic liquid and the solution of the Group 1 and/or 2 metal hydroxide in the polar solvent (preferably, water or methanol) may be mixed together in a stirred vessel followed by separation of an oil phase of reduced organic-containing acid content, a polar solvent phase containing Group 1 and/or 2 neutralization salts of the acids and a basic ionic liquid phase. It is also envisaged that the oil containing the organic-containing acids may be contacted with the basic ionic liquid and the solution of a Group 1 and/or Group 2 metal hydroxide in the polar solvent (preferably, water or methanol) in a counter-current extraction column. For example, the oil containing the organic-containing acids and an aqueous solution of the Group 1 and/or 2 metal hydroxide may be introduced at or near the bottom of the column and the basic ionic liquid at or near the top thereof. Thus, oil having a reduced acid content is removed from at or near the top of the column, basic ionic liquid from at or near the bottom of the column and an aqueous solution of Group 1 and/or 2 metal neutralization salts of the acids from an intermediate position. Alternatively, a solution of the Group 1 and/or 2 metal hydroxide in methanol may be introduced into the column, at or near the bottom thereof and, depending upon the density of the oil, a solution of the Group 1 and/or Group 2 metal neutralization salts of the acids in methanol may be removed from either at or near the top of the column with the oil of reduced organic-containing acid content being removed from an intermediate position or the oil of reduced acid content may be removed from at or near the top of the column and the solution of the Group 1 and/or Group 2 metal neutralization salts of the acids from an intermediate position.

It is also envisaged that the basic ionic liquid containing the organic-containing acids may be contacted with a $C_1$ to $C_6$ aliphatic alcohol in the presence of an esterification catalyst (for example, a heterogeneous or homogeneous esterification catalyst) under conditions effective to convert at least a portion of the acids into the corresponding esters thereof.

These ester derivatives are more volatile than the acids and hence are more readily separated from the basic ionic liquid, for example, by vaporisation at reduced pressure and at a temperature of less than 150° C.

The supported basic ionic liquid may additionally be regenerated by passing a solution of a Group 1 and/or Group 2 metal hydroxide in a polar solvent through the column such that the acids are converted into their corresponding neutralization salts and are washed off the column by the polar solvent. Suitably, the polar solvent is water or a $C_1$ to $C_6$ aliphatic alcohol or mixtures thereof. Preferably, the polar organic solvent is water, methanol or ethanol. Where the basic ionic liquid is physiosorbed onto the silica column, the basic ionic liquid should be insoluble in the polar solvent so that the basic ionic liquid is not stripped from the column. Where the polar solvent is water, the resulting waste water stream may be disposed of, for example, by being injected into a porous subterranean formation (waste water disposal zone). Where the polar organic solvent is methanol or ethanol, the solvent may be driven off from the neutralization salts at reduced pressure.

In yet another aspect of the present invention there is provided a process for removing organic acids from a crude oil and/or a crude oil distillate containing organic acids comprising the steps of:

a. contacting the crude oil and/or the crude oil distillate containing organic acids with a covalently bonded ionic liquid having the formula:

[SUPPORT-Z-Cat$^+$][X$^-$]

wherein:

SUPPORT represents a solid support, preferably selected from silica, alumina, carbon, zirconia, alumina-silica, and a zeolite;

Z is a divalent linking group;

[Cat$^+$] is a cationic moiety; and

[X$^-$] is an anion selected from alkylcarbonate (such as those described above) and hydrogen carbonate; and b. separating a crude oil and/or crude oil distillate product having reduced acidity from the solid supported ionic liquid.

The Cat$^+$ moiety may comprise or consist of a heterocyclic ring structure selected from imidazolium, pyridinium, pyrazolium, thiazolium, isothiazolinium, azathiozolium, oxothiazolium, oxazinium, oxazolium, oxaborolium, dithiazolium, triazolium, selenozolium, oxaphospholium, pyrollium, borolium, furanium, thiophenium, phospholium, pentazolium, indolium, indolinium, oxazolium, isooxazolium, isotriazolium, tetrazolium, benzofuranium, dibenzofuranium, benzothiophenium, dibenzothiophenium, thiadiazolium, pyrimidinium, pyrazinium, pyridazinium, piperazinium, piperidinium, morpholinium, pyranium, annolinium, phthalazinium, quinazolinium, quinazalinium, quinolinium, isoquinolinium, thazinium, oxazinium and azaannulenium.

Preferred [SUPPORT-Z-Cat$^+$] in accordance with the present invention may be selected from:

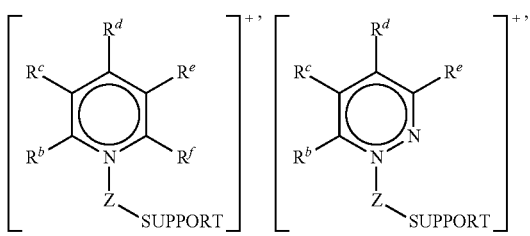
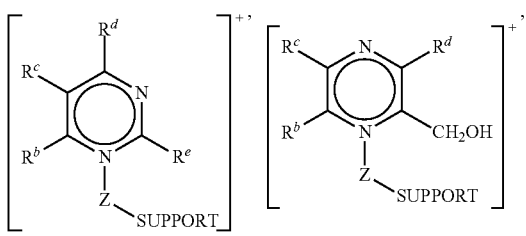
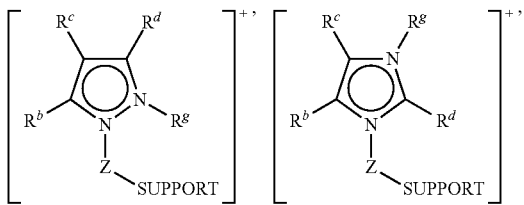
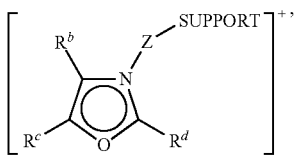
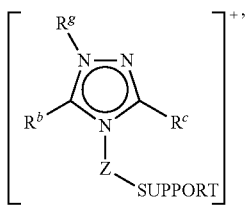
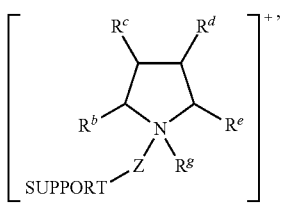
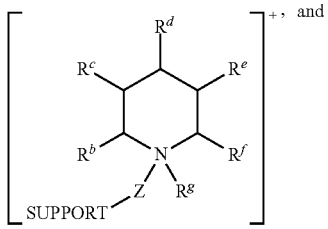
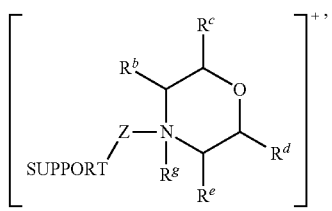

-continued wherein:
SUPPORT and Z are as defined above; and
$R^b$, $R^c$, $R^d$, $R^e$, $R^f$ and $R^g$ can be the same or different, and are each independently selected from hydrogen, a $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl, or any two of $R^b$, $R^c$, $R^d$, $R^e$ and $R^f$ attached to adjacent carbon atoms form a methylene chain —$(CH_2)_q$— wherein q is from 8 to 20.

Preferably, $R^a$, $R^b$, $R^c$, $R^d$, $R^e$, $R^f$ and $R^g$ are each independently selected from a $C_1$ to $C_{20}$ straight chain or branched alkyl group, a $C_3$ to $C_6$ cycloalkyl group, or a $C_6$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —$NO_2$, —$CO_2(C_1$ to $C_6$)alkyl, —$OC(O)(C_1$ to $C_6$)alkyl, $C_6$ to $C_{10}$ aryl and $C_7$ to $C_{10}$ alkaryl, and wherein one of $R^b$, $R^c$, $R^d$, $R^e$, $R^f$ and $R^g$ may also be hydrogen.

$R^a$ is preferably selected from $C_1$ to $C_{30}$, linear or branched, alkyl, more preferably $C_2$ to $C_{20}$ linear or branched alkyl, still more preferably, $C_2$ to $C_{10}$ linear or branched alkyl, and most preferably $R^a$ is selected from ethyl, n-butyl, n-hexyl and n-octyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_2$ to $C_{20}$ linear or branched alkyl, still more preferably, $C_2$ to $C_{10}$ linear or branched alkyl, and most preferably $C_4$ to $C_8$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_{15}$ alkoxyalkyl.

The Cat$^+$ moiety for use in the present invention may be obtained by akylation, protonation and/or acylation of a precursor selected from imidazoles, pyridines, pyrazoles, thiazoles, isothiazoles, azathiozoles, oxothiazoles, oxazines, oxazolines, oxazoboroles, dithiozoles, triazoles, selenozoles, oxaphospholes, pyrroles, boroles, furans, thiophenes, phospholes, pentazoles, indoles, indolines, oxazoles, isooxazoles, isotriazoles, tetrazoles, benzofurans, dibenzofurans, benzothiophenes, dibenzothiophenes, thiadiazoles, pyrimidines, pyrazines, pyridazines, piperazines, piperidines, morpholines, pyrans, annolines, phthalazines, quinazolines, quinazalines, quinolines, isoquinolines, thazines, oxazines, and azaannulenes.

In accordance with the present invention, the $Cat^+$ moiety may also be an acyclic organic ion.

Where the $Cat^+$ moiety is acyclic, it preferably comprises or consists of a group selected from amino amidino, imino, guanidino, phosphino, arsino, stibino, alkoxyalkyl, alkylthio, alkylseleno and phosphinimino.

Where the $Cat^+$ moiety is acyclic, [SUPPORT-Z-$Cat^+$] is preferably selected from:

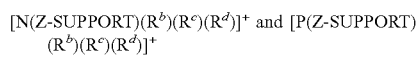

wherein: SUPPORT, Z, $R^b$, $R^c$, and $R^d$ are as defined above.

More preferably $R^b$, $R^c$ and $R^d$ may be the same or different, and are each independently selected from hydrogen, a $C_1$ to $C_{20}$, straight chain or branched alkyl group. Even more preferably, $R^b$, $R^c$ and $R^d$ are the same or different, and are each independently selected from hydrogen, a $C_1$ to $C_{10}$, straight chain or branched alkyl group.

Examples of suitable alkyl groups include methyl, ethyl, propyl, butyl, pentyl, hexyl, heptyl, octyl, nonyl and/or decyl. One preferred group of alkyl groups comprises methyl, ethyl, propyl and/or butyl.

Even more preferably, [SUPPORT-Z-$Cat^+$] is selected from:

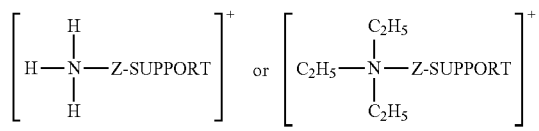

wherein: SUPPORT and Z are as defined above.

In accordance with the present invention, [SUPPORT-Z-$Cat^+$] may also be:

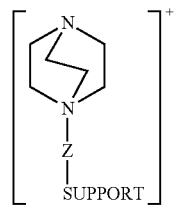

wherein: SUPPORT and Z are as defined above.

It will be readily appreciated that [SUPPORT-Z-$Cat^+$][$X^-$] may be used in accordance with one or more of the processes disclosed above and/or recycled in accordance with one or more of the regeneration processes disclosed above.

The processes of the present inventions provide a crude oil/crude oil distillate having reduced acid content.

The processes of the present inventions may be carried out on an offshore platform, in a refinery, or whilst the oil is being transported, for example, in a tanker at sea.

The present inventions will now be described further by way of example.

EXAMPLES

Test Oils
    The oils used in the examples below are as follows:
    Model oil (dodecane doped with naphthenic acids, TAN 2.00 mg/g KOH); and
    Crude oil (Chad crude oil (TAN 3.91 mg/g KOH))
Ionic Liquids
    A series of alkylcarbonate and hydrogencarbonate ionic liquids based on a tetraalkylammonium cation were chosen for the extraction of naphthenic acids from model and crude oil. The ionic liquids were produced using known methods.
Experimental Procedures
General Procedure for the Removal of Naphthenic Acids Using Bases with Model/Crude Oil in a Solid-Liquid or Liquid-Liquid Extraction
    To a sample vial containing 100 g of model/crude oil (TAN 2.00 mg KOH/g and TAN 3.91 respectively) was added the specified mass of ionic liquid. The resulting mixture was stirred for the desired length of time at the specified temperature. For the liquid-liquid and solid-liquid extractions, the sample was centrifuged at 3000 rpm for 10 minutes. After separation of the phases, ~5.00-10.00 g of the model/crude oil was taken and analysed by titration.
General Procedure for the Recycling of the Ionic Liquids and the Solid Systems
    After phase separation, to the resultant lower layer was added 10 ml of water saturated with $CO_2$. This was stirred for ten minutes and then the cloudy solution was centrifuged at 3000 rpm for 60 minutes. For the ionic liquid extractions the upper oil phase was removed and the lower aqueous phase was dried to leave the ionic liquid which was recycled according to the general procedure above. For the supported ionic liquid systems both the oil and aqueous phase were removed before drying of the solid prior to recycle.
Unsupported Basic Ionic Liquids
    Two basic ionic liquids derived from methylcarbonate and hydrogencarbonate were tested with the crude oil sample, and the results are shown in Table 1 below.

TABLE 1

Resultant TAN number upon extraction of ~100 g of crude oil with [$N_{1,2,2,2}$][$MeCO_3$] and [$N_{1,2,2,2}$] [$HCO_3$]

| Entry | IL | IL mass (g) | mMoles of IL | OIL/IL Mass ratio | Crude Oil Resultant TAN |
|---|---|---|---|---|---|
| 1 | [$N_{1,2,2,2}$][$MeCO_3$] | 1.38 | 7.2 | 72 | <0.1 |
| 2 | [$N_{1,2,2,2}$][$HCO_3$] | 1.27 | 7.2 | 79 | <0.1 |

The results clearly demonstrate that for both the methyl and hydrogencarbonate systems an IL:OIL mass ratio of ~1:75 is capable of reducing naphthenic acids in the crude to below 0.1 mg/g.

Similar results were obtained for tests using the [$N_{1,4,4,4}$][$HCO_3$] [$N_{1,4,4,4}$][$MeCO_3$] ionic liquids.
Recycling of Unsupported Basic Ionic Liquids
    The application of ionic liquids as reagents to remove naphthenic acids from oil was further explored by subjecting these reagents to recycle.
    Table 2 (below) demonstrates the advantages of regeneration via a carbonic acid wash in accordance with an aspect of the present inventions, versus non-regeneration. Two basic ionic liquids derived from methyl and hydrogencarbonate were used.

TABLE 2

Comparison of regenerative and non-regenerative recycle of [N$_{1,2,2,2}$][MeCO$_3$] and [N$_{1,2,2,2}$] [HCO$_3$] on resulting TAN numbers in crude oil

| Ionic liquid | Non-regenerated (mg/g KOH) | | Carbonic wash (mg/g KOH) | |
|---|---|---|---|---|
| 7.2 mmol | 1 | 2 | 1 | 2 |
| [N$_{1,2,2,2}$][MeCO$_3$] | <0.1 | 3.9 | <0.1 | 0.45 |
| [N$_{1,2,2,2}$][HCO$_3$] | <0.1 | 3.87 | <0.1 | 0.23 |

In both ionic liquids studied the resulting TAN number shows no decrease where the alkylcarbonate ionic liquid is recycled without regeneration. In clear contrast, the use of carbonic acid regeneration of the alkylcarbonate ionic liquids results in good activity being retained.

The results demonstrate a cheap and facile process for basic ionic liquid recycling.

Supported Basic Ionic Liquids

[N$_{1,2,2,2}$][HCO$_3$], [N$_{1,2,2,2}$][MeCO$_3$] and [N$_{1,4,4,4}$][MeCO$_3$] ionic liquids were supported onto silica (IL:SiO$_2$ mass 1:2) by wet impregnation and its performance compared at various ionic liquid to oil mass ratios (see Table 3 below).

TABLE 3

Resultant TAN number upon extraction of ~100 g of model oil at 20° C. for different silica supported ionic liquids

| Entry | Ionic liquid | IL mass (g) | mMoles of IL | OIL/IL Mass ratio | Model Oil Resultant TAN |
|---|---|---|---|---|---|
| 1 | [N$_{1,2,2,2}$][HCO$_3$] | 0.635 | 3.5 | 157 | <0.1 |
| 2 | [N$_{1,2,2,2}$][MeCO$_3$] | 0.69 | 3.6 | 145 | <0.1 |
| 3 | [N$_{1,4,4,4}$][MeCO$_3$] | 0.98 | 3.6 | 102 | <0.1 |

The results in table 3 demonstrate that supported basic ionic liquids can also be used for naphthenic acid removal.

Covalently Bound Ionic Liquids

The use of covalently bound ionic liquids for solid adsorption of naphthenic acids has also been explored using covalently bound ionic liquids, such as an alkylammonium propyl silicas (see Structure 1 below), results of which are shown in Table 4 (also below).

Structure 1: Structure of the Covalently 'Tethered' Aminopropyl Silica

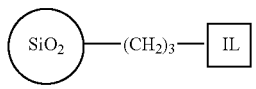

As was noted with the physisorbed supported basic ionic liquids, the chemisorbed supported ionic liquids have also been shown to reduce naphthenic acids content in both model oil and crude oil systems. A major advantage of this system is that the aminopropyl silicas negate reagent leaching into the bulk oil.

TABLE 4

Remaining TAN number after extraction of the liquid phase when using covalently bound basic ionic liquids

| Supported IL (0.25 g) | N loading (mmol g$^{-1}$) | TAN Model Oil* | TAN Crude Oil* |
|---|---|---|---|
| [SiO$_2$—NH$_3$] [HCO$_3$] | 1.01 | <0.1 | 3.37 |
| [SiO$_2$—NEt$_3$] [HCO$_3$] | 0.98 | 0.18 | 3.13 |

*reactions conducted using 7 g of oil

Recycling of Basic Solids

Similar to the basic ionic liquid recycle experiments, regeneration of the chemisorbed basic ionic liquid can also be achieved with the use of carbonic acid (see Table 5 below).

TABLE 5

Recycle of the covalently bound basic ionic liquid/model oil using carbonic wash

| Silica | Non-regenerated | | Carbonic wash | |
|---|---|---|---|---|
| 0.25 g | TAN 1 | TAN 2 | TAN 1 | TAN 2 |
| [SiO$_2$—NEt$_3$] [HCO$_3$] | 0.12 | 1.83 | 0.17 | 0.31 |

Bound IL [SiO$_2$—NEt$_3$][HCO$_3$] shows similar activity after regeneration compared to the initial experiments. In contrast without regeneration the extraction ability of these solids decreases significantly.

CONCLUSION

The use of the selected alkylcarbonate or hydrogencarbonate basic ionic liquids of the present inventions allows for TAN levels in crude oil to be reduced to <0.1 with OIL/IL ratios as high as ~80.

Solid supporting of these ionic liquids, such as for example alkylammonium and alkylcarbonates, also allows a significant naphthenic acid reduction to be achieved.

The use of covalently bound basic ionic liquids can also be employed as supported reagents to remove naphthenic acids from crude oil.

Both the supported ionic liquid and covalently bound basic ionic liquids reagents can be effectively recycled after use by simple regeneration using carbonic acid.

The invention claimed is:

1. A process for removing organic acids from at least one of a crude oil and a crude oil distillate containing organic acids comprising the steps of:
   (i) contacting at least one of the crude oil and the crude oil distillate containing organic acids with a supported basic ionic liquid having a basic anion selected from hydrogencarbonate or alkylcarbonate, wherein the ionic liquid and at least one of the crude oil and the crude oil distillate are contacted in a mass ratio of from greater than 1:40; and
   (ii) obtaining at least one of a crude oil and a crude oil distillate product having reduced acidity which is separated from the supported basic ionic liquid.

2. A process according to claim 1, wherein the ionic liquid and at least one of the crude oil and the crude oil distillate are contacted in a mass ratio of from greater than 1:40 to up to 1:300.

3. A process according to claim 1, wherein the basic anion is selected from alkylcarbonate anions, wherein the alkyl group of the alkylcarbonate anion comprises from 1 to 20 carbon atoms.

4. A process according to claim 3, wherein the alkyl group is selected from at least one member of a group consisting of: methyl, ethyl, propyl, butyl, pentyl, hexyl, heptyl, octyl, nonyl and decyl.

5. A process according to claim 1, wherein the support is selected from silica, alumina, carbon, zirconia, alumina-silica, or a zeolite.

6. A process according to claim 1, wherein the ionic liquid is adsorbed onto the support in an ionic liquid support mass ratio of from 10:1 to 1:10.

7. A process for removing organic acids from at least one of a crude oil and a crude oil distillate containing organic acids comprising the steps of:
 (i) contacting at least one of the crude oil and the crude oil distillate containing organic acids with a basic ionic liquid having a basic anion selected from hydrogencarbonate or alkylcarbonate, and further wherein the ionic liquid and at least one of the crude oil and the crude oil distillate are contacted in a mass ratio of from greater than 1:40; and
 (ii) obtaining at least one of a crude oil and a crude oil distillate product having reduced acidity which is separated from the basic ionic liquid.

8. A process according to claim 7, wherein the basic anion is selected from alkylcarbonate anions, wherein the alkyl group of the alkylcarbonate anion comprises from 1 to 20 carbon atoms.

9. A process according claim 7, wherein the organic acids are naphthenic acids.

10. A process according claim 7, wherein the basic ionic liquid comprises a cation selected or derived from the group consisting of: ammonium, azaannulenium, azathiazolium, benzimidazolium, benzofuranium, benzotriazolium, borolium, cinnolinium, diazabicyclodecenium, diazabicyclononenium, diazabicyclo-undecenium, dithiazolium, furanium, imidazolium, indazolium, indolinium, indolium, morpholinium, oxaborolium, oxaphospholium, oxazinium, oxazolium, iso-oxazolium, oxothiazolium, pentazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenozolium, sulfonium, tetrazolium, isothiadiazolium, thiazinium, thiazolium, thiophenium, triazadecenium, triazinium, triazolium, iso-triazolium, and a cation selected from the group consisting of:

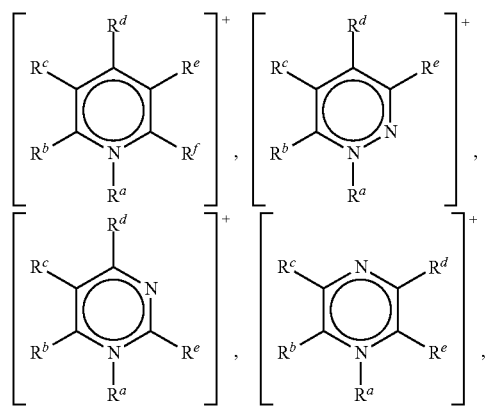

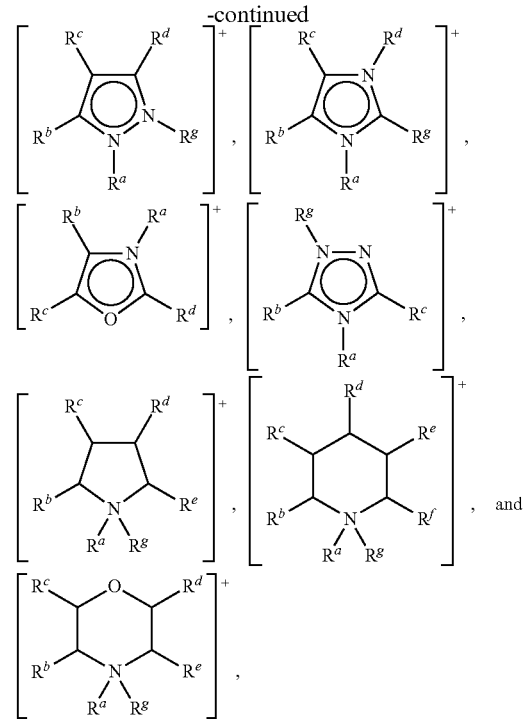

wherein: $R^a$, $R^b$, $R^c$, $R^d$, $R^e$, $R^f$ and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or are substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —NO$_2$, $C_6$ to $C_{10}$ aryl and $C_7$ to $C_{10}$ alkaryl, —CO$_2$($C_1$ to $C_6$)alkyl, —OC(O)($C_1$ to $C_6$)alkyl, or any two of $R^b$, $R^c$, $R^d$, $R^e$ and $R^f$ attached to adjacent carbon atoms form a methylene chain —(CH$_2$)$_q$— wherein q is from 3 to 6, or a cation is selected from the group consisting of:

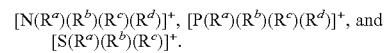

11. A process according to claim 7, wherein the ionic liquid additionally comprises a basic cation represented by the formula:

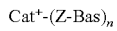

wherein:
 Cat$^+$ is a positively charged moiety;
 Bas is a basic moiety;
 Z is a covalent bond joining Cat$^+$ and Bas, or is a divalent linking group; and
 n is an integer of from 1 to 3.

12. A process according to claim 11, wherein Cat$^+$ represents a heterocyclic ring structure selected from at least one member of a group consisting of: imidazolium, pyridinium, pyrazolium, thiazolium, isothiazolinium, azathiozolium, oxothiazolium, oxazinium, oxazolium, oxaborolium, dithiozolium, triazolium, selenozolium, oxaphospholium, pyrollium, borolium, furanium, thiophenium, phospholium, pentazolium, indolium, indolinium, oxazolium, isooxazolium, isotriazolium, tetrazolium, benzofuranium, dibenzofuranium, benzothiophenium, dibenzothiophenium, thiadiazolium, pyrimidinium, pyrazinium, pyridazinium, piperazinium, piperidinium, morpholenium, pyranium, annolinium, phthalazinium, quinazolinium, quinazalinium, quinolinium, isoquinolinium, thazinium, oxazinium and azaannulenium.

13. A process according to claim 11, wherein Cat$^+$-Z-Bas is selected from:

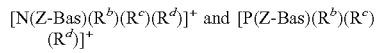

wherein: Bas and Z are as defined in claim 11 and each of R$^b$, R$^c$, and R$^d$ are independently selected from methyl and ethyl.

14. A process according to claim 7, wherein the material to be deacidified is crude oil or a crude oil distillate selected from liquefied petroleum gas, gasoline, gas oil, diesel, jet fuel, kerosene, home heating oil, and mixtures thereof.

15. A process according to claim 7, wherein at least one of the crude oil and the crude oil distillate having reduced acid content is separated from the basic ionic liquid containing organic acids by means of a liquid-liquid extraction.

16. A process according claim 7, further comprising recovering the basic ionic liquid from the organic acids by way of a regeneration process, wherein the regeneration process comprises:
 a) contacting the basic ionic liquid with a carbonic acid, having a pKa of less than 6.75.

17. A process according to claim 16, wherein the pKa of the acid is less than 6.25.

18. A process according to claim 7, for removing organic acids from at least of one of the crude oil and the crude oil distillate containing organic acids comprising the steps of:
 (i) contacting at least one of the crude oil and the crude oil distillate containing organic acids with a supported ionic liquid having the formula:

[SUPPORT-Z-Cat$^+$][X$^-$]

wherein:
 SUPPORT represents a solid support;
 Z is a covalent bond joining Cat$^+$ and Bas, or is a divalent linking group;
 [Cat$^+$] is a cationic moiety; and
 [X$^-$] is an anion selected from alkylcarbonates and hydrogen carbonate; and
 (ii) separating at least one of the crude oil and the crude oil distillate product having reduced acidity from the solid supported ionic liquid wherein [SUPPORT-Z-Cat$^+$] is selected from:

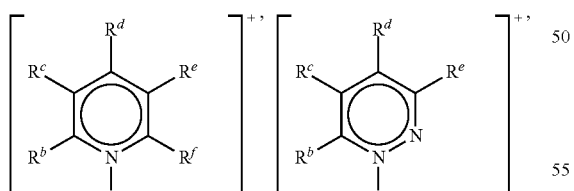

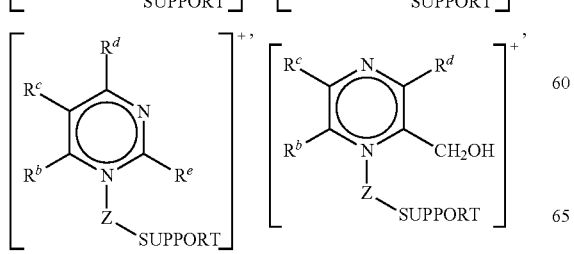

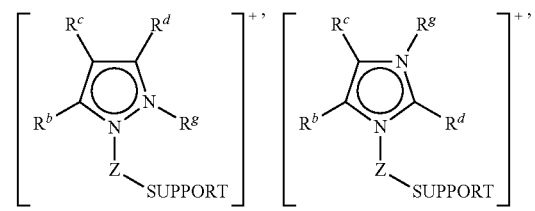

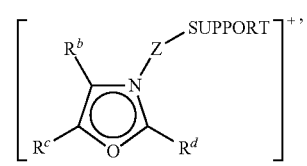

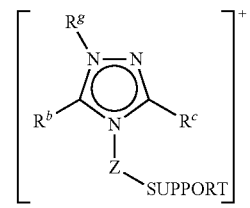

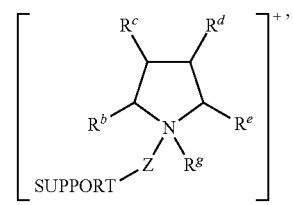

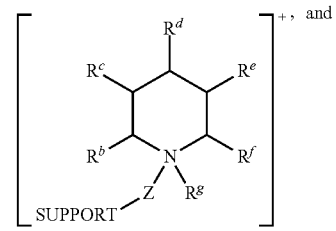

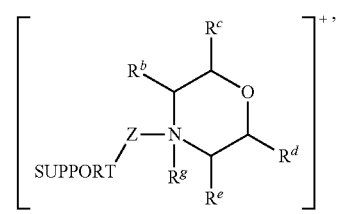

wherein: R$^b$, R$^c$, R$^d$, R$^e$, R$^f$ and R$^g$ can be the same or different, and are each independently selected from hydrogen, a C$_1$ to C$_{40}$, straight chain or branched alkyl group, a C$_3$ to C$_8$ cycloalkyl group, or a C$_6$ to C$_{10}$ aryl group, wherein said alkyl, cycloalkyl or aryl groups are unsubstituted or may be substituted by one to three groups selected from: C$_1$ to C$_6$ alkoxy, C$_6$ to C$_{10}$ aryl, CN, OH, NO$_2$, C$_7$ to C$_{30}$ aralkyl and C$_7$ to C$_{30}$ alkaryl, or any two of R$^b$, R$^c$, R$^d$, R$^e$ and R$^f$ attached to adjacent carbon atoms form a methylene chain —(CH$_2$)$_q$— wherein q is from 8 to 20, or an acyclic moiety, and comprises or consists of a group selected from amino amidino, imino, guanidino, phosphino, arsino, stibino, alkoxyalkyl, alkylthio, alkylseleno and phosphinimino, and is selected from:

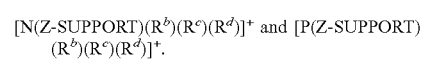

19. A process according to claim 18, wherein [SUPPORT-Z-Cat$^+$] is:

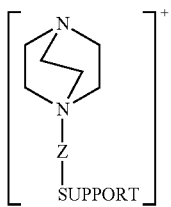

wherein: SUPPORT and Z are as defined in claim 18.

20. A process according to claim 18, wherein the solid support is selected from at least one member of a group consisting of: silica, alumina, carbon, zirconia, alumina-silica, and a zeolite.

21. A process according claim 10, wherein: [Cat$^+$] is selected from:

$$[N(R^a)(R^b)(R^c)(R^d)]^+,$$

and wherein $R^a$, $R^b$, $R^c$ and $R^d$ are each independently selected from $C_1$ to $C_8$ alkyl.

22. A process according claim 16, wherein the regeneration process further comprises the steps of:

b) contacting the mixture of step a) with a solvent which is immiscible with the basic ionic liquid; and c) separating the solvent from the ionic liquid.

23. A crude oil/crude oil distillate having reduced acid content, the crude oil/crude oil distillate including a basic ionic liquid as defined in claim 7 and produced in accordance with the processes of claim 7.

* * * * *